(12) United States Patent
Woulfe et al.

(10) Patent No.: US 12,728,254 B2
(45) Date of Patent: Sep. 8, 2026

(54) BLOOD PUMP CONTROL USING MOTOR VOLTAGE MEASUREMENT

(71) Applicant: Boston Scientific Scimed, Inc., Maple Grove, MN (US)

(72) Inventors: Marit Elisabeth Woulfe, Ramsey, MN (US); Qian Liu, Plymouth, MN (US); John O'Donnell, Tipperary (IE); Ronald Gunnels, Rogersville, MO (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 203 days.

(21) Appl. No.: 18/388,118

(22) Filed: Nov. 8, 2023

(65) Prior Publication Data

US 2024/0165391 A1 May 23, 2024

Related U.S. Application Data

(60) Provisional application No. 63/427,527, filed on Nov. 23, 2022.

(51) Int. Cl.
*A61M 60/122* (2021.01)
*A61M 60/216* (2021.01)
(Continued)

(52) U.S. Cl.
CPC ........ *A61M 60/122* (2021.01); *A61M 60/216* (2021.01); *A61M 60/422* (2021.01);
(Continued)

(58) Field of Classification Search
CPC .. A61M 61/148; A61M 60/13; A61M 60/237; A61M 60/414; A61M 60/422;
(Continued)

(56) References Cited

U.S. PATENT DOCUMENTS 5,527,159 A 6/1996 Bozeman, Jr. et al.
5,692,882 A 12/1997 Bozeman, Jr. et al.
(Continued)

FOREIGN PATENT DOCUMENTS

CN 101983732 A 3/2011
EP 1267958 B1 * 11/2004 .......... A61M 60/411
(Continued)

OTHER PUBLICATIONS

US 9,067,007 B2, 06/2015, Tanner et al. (withdrawn)
(Continued)

*Primary Examiner* — Jon Eric C Morales
(74) *Attorney, Agent, or Firm* — Seager, Tufte & Wickhem LLP

(57) ABSTRACT

A percutaneous circulatory support device includes an impeller, a motor configured to rotate the impeller to cause blood to flow through the percutaneous circulatory support device, and a controller operably coupled to the motor. The controller is configured to determine a vascular pressure within a patient, a working voltage applied to the motor to cause the motor to rotate the impeller, a working speed of the motor caused by providing the working voltage to the motor, a blood flow parameter based on the vascular pressure, the working voltage, and the working speed, and a cardiac performance parameter based on the blood flow parameter.

20 Claims, 3 Drawing Sheets

(51) Int. Cl.

*A61M 60/422* (2021.01)
*A61M 60/531* (2021.01)
*A61M 60/538* (2021.01)
*A61M 60/90* (2021.01)

(52) U.S. Cl.

CPC ........ *A61M 60/531* (2021.01); *A61M 60/538* (2021.01); *A61M 60/90* (2021.01); *A61M 2205/3303* (2013.01); *A61M 2205/3331* (2013.01); *A61M 2205/3365* (2013.01); *A61M 2230/005* (2013.01); *A61M 2230/30* (2013.01)

(58) Field of Classification Search

CPC .............. A61M 60/808; A61M 60/216; A61M 60/857; A61M 60/824; A61M 60/825; A61M 60/174; A61M 60/826; A61M 2205/3334; A61M 60/81; A61M 60/135; A61M 60/829; A61M 60/419; A61M 60/538; A61M 60/546; A61M 60/205; A61M 60/865; A61M 60/531; A61M 60/508; A61M 60/411; A61M 60/178; A61M 60/50; A61M 25/0082; A61M 60/82; A61M 60/812; A61M 25/0068; A61M 25/0069; A61M 60/585; A61M 2205/33665; A61M 25/0074; A61M 60/416; A61M 60/827; A61M 60/221; A61M 60/818; A61M 2205/0266; A61M 60/232; A61M 60/523; A61M 2205/3344; A61M 60/816; A61M 2205/18; A61M 2205/502; A61M 2205/52; A61M 2230/30; A61M 60/896; A61M 60/554; A61M 60/861; A61M 60/88; A61M 2210/125; A61M 60/40; A61M 2205/50; A61M 2207/00; A61M 2210/127; A61M 60/139; A61M 60/211; A61M 60/253; A61M 60/405; A61M 60/196; A61M 2205/3317; A61M 60/122; A61M 60/515; A61M 60/804; A61M 60/822; A61M 1/3659; A61M 2205/3606; A61M 2205/366; A61M 2205/3666; A61M 25/09; A61M 60/577; A61M 2205/0211; A61M 2205/3331; A61M 2205/826; A61M 60/562; A61M 60/814; A61M 60/859; A61M 60/867; A61M 1/02; A61M 1/3624; A61M 1/3627; A61M 1/3692; A61M 1/3693; A61M 2205/0238; A61M 2205/04; A61M 2205/12; A61M 2205/13; A61M 2205/32; A61M 2205/3306; A61M 2205/3351; A61M 2205/3355; A61M 2205/3389; A61M 2205/3393; A61M 2209/084; A61M 2230/04; A61M 5/142; A61M 60/226; A61M 60/403; A61M 60/833; A61M 60/878; A61M 60/864; A61M 1/362265; A61M 1/63; A61M 2205/0272; A61M 2205/103; A61M 2205/33; A61M 2205/702; A61M 60/117; A61M 60/165; A61M 60/17; A61M 60/592; A61M 1/1524; A61M 1/155; A61M 2005/1402; A61M 2025/0006; A61M 2025/0073; A61M 2205/0283; A61M 2205/17; A61M 2205/3303; A61M 2205/3327; A61M 2205/3368; A61M 2205/3507; A61M 2205/3515; A61M 2205/3561; A61M 2205/584; A61M 2205/018; A61M 2206/10; A61M 2230/06; A61M 2230/20; A61M 2230/208; A61M 2230/43; A61M 25/04; A61M 5/14212; A61M 5/14236; A61M 5/14276; A61M 5/172; A61M 5/1723; A61M 60/113; A61M 60/242; A61M 60/279; A61M 60/33; A61M 60/408; A61M 60/871; A61M 60/873; A61M 60/876; A61M 60/888; A61M 60/90; A61M 2205/0216; A61M 2205/10; A61M 2205/3358; A61M 60/00; A61M 60/126; A61M 60/268; A61M 60/295; A61M 60/569; A61M 60/855; F04D 29/181; F04D 3/02; F04D 29/247; F04D 29/528; F04D 3/00; F04D 3/005; F04D 29/242; F04D 29/42; F04D 29/026; F04D 29/183; F04D 29/542; F04D 19/02; F04D 29/382; F04D 29/526; F04D 29/0476; F04D 29/043; F04D 1/00; F04D 25/06; F04D 29/046; F04D 7/00; F04D 13/02; F04D 13/021; F04D 13/024; F04D 13/026; F04D 13/06; F04D 13/0633; F04D 13/064; F04D 29/0467; F04D 29/18; F04D 29/20; F04D 29/548; F04D 29/60; F04D 29/605; F04D 29/669; F04D 13/0646; F04D 25/0066; F04D 25/02; F04D 29/041; F04D 29/042

See application file for complete search history.

(56) References Cited

U.S. PATENT DOCUMENTS

| | | | |
|---|---|---|---|
| 5,947,892 | A | 9/1999 | Benkowski et al. |
| 6,135,729 | A | 10/2000 | Aber |
| 6,139,487 | A | 10/2000 | Siess |
| 6,176,822 | B1 | 1/2001 | Nix et al. |
| 7,841,976 | B2 | 11/2010 | McBride et al. |
| 7,927,068 | B2 | 4/2011 | McBride et al. |
| 7,972,122 | B2 | 7/2011 | Larose et al. |
| 8,376,707 | B2 | 2/2013 | McBride et al. |
| 8,591,393 | B2 | 11/2013 | Walters et al. |
| 8,597,170 | B2 | 12/2013 | Walters et al. |
| 8,684,904 | B2 | 4/2014 | Campbell et al. |
| 8,721,517 | B2 | 5/2014 | Zeng et al. |
| 8,992,163 | B2 | 3/2015 | McBride et al. |
| 9,072,825 | B2 | 7/2015 | Pfeffer et al. |
| 9,089,635 | B2 | 7/2015 | Reichenbach et al. |
| 9,138,518 | B2 | 9/2015 | Yuen et al. |
| 9,162,017 | B2 | 10/2015 | Evans et al. |
| 9,308,302 | B2 | 4/2016 | Zeng |
| 9,308,304 | B2 | 4/2016 | Peters et al. |
| 9,327,067 | B2 | 5/2016 | Zeng et al. |
| 9,364,592 | B2 | 6/2016 | McBride et al. |
| 9,364,593 | B2 | 6/2016 | McBride et al. |
| 9,381,288 | B2 | 7/2016 | Schenck et al. |
| 9,421,311 | B2 | 8/2016 | Tanner et al. |
| 9,446,179 | B2 | 9/2016 | Keenan et al. |
| 9,656,010 | B2 | 5/2017 | Burke |
| 9,675,740 | B2 | 6/2017 | Zeng et al. |
| 9,717,833 | B2 | 8/2017 | McBride et al. |
| 9,770,543 | B2 | 9/2017 | Tanner et al. |
| 9,872,947 | B2 | 1/2018 | Keenan et al. |
| 9,895,476 | B2 | 2/2018 | Larose et al. |
| 9,907,890 | B2 | 3/2018 | Muller |
| 9,956,332 | B2 | 5/2018 | Larose et al. |
| 9,962,475 | B2 | 5/2018 | Yuen et al. |
| 9,964,115 | B2 | 5/2018 | Scheckel |
| 10,029,037 | B2 | 7/2018 | Muller et al. |
| 10,039,872 | B2 | 8/2018 | Zeng et al. |
| 10,071,192 | B2 | 9/2018 | Zeng |
| 10,086,121 | B2 | 10/2018 | Fitzgerald et al. |
| 10,105,475 | B2 | 10/2018 | Muller |
| 10,117,980 | B2 | 11/2018 | Keenan et al. |
| 10,149,932 | B2 | 12/2018 | McBride et al. |

(56) References Cited

U.S. PATENT DOCUMENTS 10,215,187 B2 2/2019 McBride et al.
10,232,099 B2 3/2019 Peters et al.
10,251,985 B2 4/2019 Larose et al.
10,251,986 B2 4/2019 Larose et al.
10,426,879 B2 10/2019 Farnan
10,449,932 B2 10/2019 Schaeuble et al.
10,478,539 B2 11/2019 Pfeffer et al.
10,478,540 B2 11/2019 Scheckel et al.
10,525,178 B2 1/2020 Zeng
10,543,302 B2 1/2020 Reyes et al.
10,576,192 B2 3/2020 Muller et al.
10,576,193 B2 3/2020 Tanner et al.
10,610,627 B2 4/2020 Hayward
10,688,232 B2 6/2020 Voskoboynikov et al.
10,709,829 B2 7/2020 Muller
10,709,830 B2 7/2020 Tanner et al.
10,765,789 B2 9/2020 Zeng et al.
10,765,791 B2 9/2020 Moyer et al.
10,780,208 B2 9/2020 Siess et al.
10,786,610 B2 9/2020 Zeng
10,799,624 B2 10/2020 Pfeffer et al.
10,835,654 B2 11/2020 Harjes et al.
10,842,921 B2 11/2020 Siess et al.
10,864,308 B2 12/2020 Muller et al.
10,864,309 B2 12/2020 McBride et al.
10,874,783 B2 12/2020 Pfeffer et al.
10,894,115 B2 1/2021 Pfeffer et al.
10,918,774 B2 2/2021 Stanfield et al.
10,960,116 B2 3/2021 Yuen et al.
10,960,118 B2 3/2021 Sunagawa
10,980,927 B2 4/2021 Pfeffer et al.
11,058,865 B2 7/2021 Fitzgerald et al.
11,123,539 B2 9/2021 Pfeffer et al.
11,129,978 B2 9/2021 Pfeffer et al.
11,167,124 B2 11/2021 Pfeffer et al.
11,229,786 B2 1/2022 Zeng et al.
11,235,138 B2 2/2022 Gross-Hardt et al.
11,253,693 B2 2/2022 Pfeffer et al.
11,260,213 B2 3/2022 Zeng et al.
11,273,301 B2 3/2022 Pfeffer et al.
11,298,524 B2 4/2022 El Katerji et al.
11,311,712 B2 4/2022 Zeng et al.
11,338,124 B2 5/2022 Pfeffer et al.
11,357,967 B2 6/2022 Zeng et al.
11,357,968 B2 6/2022 El Katerji et al.
11,400,276 B2 8/2022 Chopra et al.
11,497,896 B2 11/2022 Tanner et al.
11,517,736 B2 12/2022 Earles et al.
11,529,062 B2 12/2022 Moyer et al.
11,583,659 B2 2/2023 Pfeffer et al.
11,628,294 B2 4/2023 Chopra et al.
11,708,833 B2 7/2023 McBride et al.
11,754,075 B2 9/2023 Schuelke et al.
11,786,700 B2 10/2023 Pfeffer et al.
2008/0114339 A1 5/2008 McBride et al.
2009/0060743 A1 3/2009 McBride et al.
2017/0296725 A1 10/2017 Peters et al.
2018/0303990 A1 10/2018 Siess et al.
2018/0311423 A1 11/2018 Zeng et al.
2018/0353667 A1* 12/2018 Moyer ................ A61M 60/237
2020/0222607 A1 7/2020 El Katerji et al.
2020/0360582 A1 11/2020 Siess et al.
2021/0015982 A1 1/2021 Kerkhoffs et al.
2021/0038785 A1 2/2021 Siess et al.
2021/0038793 A1 2/2021 Moyer et al.
2021/0106810 A1 4/2021 Pfeffer et al.
2022/0134082 A1 5/2022 Pfeffer et al.
2022/0167862 A1* 6/2022 Edelman .............. A61B 5/0215
2022/0184375 A1 6/2022 Tuval et al.
2022/0241579 A1 8/2022 Liu et al.

FOREIGN PATENT DOCUMENTS

EP 847767 B1 2/2005
EP 2301598 B1 7/2017
EP 3352808 B1 9/2023
JP 2022517619 A 3/2022

OTHER PUBLICATIONS

International Search Report and Written Opinion for International Application No. PCT/US2023/037030, dated Mar. 19, 2024, (17 pages).

* cited by examiner

BLOOD PUMP CONTROL USING MOTOR VOLTAGE MEASUREMENT

CROSS-REFERENCE TO RELATED PATENT APPLICATIONS

This application claims priority to U.S. Provisional Application No. 63/427,527, filed Nov. 23, 2022, which is herein incorporated by reference in its entirety.

TECHNICAL FIELD

The present disclosure relates to percutaneous circulatory support systems. More specifically, the disclosure relates to percutaneous circulatory support devices that determine one or more cardiac performance parameters of a patient.

BACKGROUND

Percutaneous circulatory support devices, or blood pumps, can provide transient support for up to approximately several weeks in patients with compromised heart function or cardiac output. However, when using such devices it is typically difficult for medical practitioners to determine if and when the amount of support provided such devices should be modified and when treatment should conclude. To assist the medical practitioners, estimates of cardiac performance are provided by some devices. These estimates are derived in part from operating parameters of these devices, specifically motor speed and torque. The motors of percutaneous circulatory support devices typically lack onboard speed sensors (due to size constraints) and, as a result, motor speed is typically estimated from fluctuations in motor current. Such current is typically measured using a series of resistors and amplifiers. These additional parts may increase both the complexity and cost of these devices. Moreover, such current measurements may be error prone. Accordingly, there is a need for improved devices.

SUMMARY

In an Example 1, a percutaneous circulatory support device comprises: an impeller; a motor configured to rotate the impeller to cause blood to flow through the percutaneous circulatory support device; and a controller operably coupled to the motor, the controller being configured to determine: a vascular pressure within a patient; a working voltage applied to the motor to cause the motor to rotate the impeller; a working speed of the motor caused by providing the working voltage to the motor; a blood flow parameter based on the vascular pressure, the working voltage, and the working speed; and a cardiac performance parameter based on the blood flow parameter.

In an Example 2, the percutaneous circulatory support system of Example 1, further comprising a pressure sensor operably coupled to the controller, wherein the controller is configured to determine the vascular pressure within the patient via the pressure sensor.

In an Example 3, the percutaneous circulatory support system of either of Examples 16 or 2, wherein the controller determines the blood flow parameter by using a mathematical function comprising the vascular pressure, the working voltage, and the working speed.

In an Example 4, the percutaneous circulatory support system of Example 19, wherein the mathematical function comprises a square of the vascular pressure.

In an Example 5, the percutaneous circulatory support system of either of Examples 19 or 4, wherein the mathematical function comprises a square of the working voltage.

In an Example 6, the percutaneous circulatory support system of any of Examples 19-5, wherein the mathematical function comprises a square of the working speed.

In an Example 7, the percutaneous circulatory support system of any of Examples 19-6, wherein the mathematical function comprises a product of the vascular pressure and the working voltage.

In an Example 8, the percutaneous circulatory support system of any of Examples 19-7, wherein the mathematical function comprises a product of the vascular pressure and the working speed.

In an Example 9, the percutaneous circulatory support system of any of Examples 19-8, wherein the mathematical function comprises a product of the working voltage and the working speed.

In an Example 10, the percutaneous circulatory support system of any of Examples 19-9, wherein the mathematical function comprises a product of the vascular pressure, the working voltage, and the working speed.

In an Example 11, a method of operating a percutaneous circulatory support device, the device comprising an impeller, a motor configured to rotate the impeller to cause blood flow within the patient, and a controller operably coupled to the motor, the method comprising: determining, via the controller, a vascular pressure within a patient; determining, via the controller, a working voltage applied to the motor to cause the motor to rotate the impeller; determining, via the controller, a working speed of the motor caused by providing the working voltage to the motor; determining, via the controller, a blood flow parameter based on the vascular pressure, the working voltage, and the working speed; and determining, via the controller, a cardiac performance parameter based on the blood flow parameter.

In an Example 12, the method of Example 27, further comprising modifying operation of the percutaneous circulatory support device based on the cardiac performance parameter.

In an Example 13, the method of either of Examples 27 or 12, further comprising determining, via the controller, contractibility of cardiac function of the patient by varying the working speed of the motor.

In an Example 14, the method of any of Examples 27-13, further comprising segmenting, via the controller, waveforms of the working voltage.

In an Example 15, the method of any of Examples 27-14, wherein determining, via the controller, the blood flow parameter comprises using a mathematical function comprising the vascular pressure, the working voltage, and the working speed.

In an Example 16, a percutaneous circulatory support device comprises: a housing configured to be positioned within a patient; an impeller carried within the housing; a motor configured to rotate the impeller relative to the housing to cause blood to flow through the housing; and a controller operably coupled to the motor, the controller being configured to determine: a vascular pressure within the patient; a working voltage applied to the motor to cause the motor to rotate the impeller; a working speed of the motor caused by providing the working voltage to the motor; a blood flow parameter based on the vascular pressure, the working voltage, and the working speed; and a cardiac performance parameter based on the blood flow parameter.

In an Example 17, the percutaneous circulatory support system of Example 1, further comprising a pressure sensor operably coupled to the controller, wherein the controller is configured to determine the vascular pressure within the patient via the pressure sensor.

In an Example 18, the percutaneous circulatory support system of Example 1, wherein the motor comprises a plurality of motor windings, and the controller is configured to determine the working speed of the motor based on voltage fluctuations in the plurality of motor windings.

In an Example 19, the percutaneous circulatory support system of Example 1, wherein the controller determines the blood flow parameter by using a mathematical function comprising the vascular pressure, the working voltage, and the working speed.

In an Example 20, the percutaneous circulatory support system of Example 4, wherein the mathematical function comprises a square of the vascular pressure.

In an Example 21, the percutaneous circulatory support system of Example 4, wherein the mathematical function comprises a square of the working voltage.

In an Example 22, the percutaneous circulatory support system of Example 4, wherein the mathematical function comprises a square of the working speed.

In an Example 23, the percutaneous circulatory support system of Example 4, wherein the mathematical function comprises a product of the vascular pressure and the working voltage.

In an Example 24, the percutaneous circulatory support system of Example 4, wherein the mathematical function comprises a product of the vascular pressure and the working speed.

In an Example 25, the percutaneous circulatory support system of Example 4, wherein the mathematical function comprises a product of the working voltage and the working speed.

In an Example 26, the percutaneous circulatory support system of Example 4, wherein the mathematical function comprises a product of the vascular pressure, the working voltage, and the working speed.

In an Example 27, a method of operating a percutaneous circulatory support device positioned in a patient, the device comprising an impeller, a motor configured to rotate the impeller to cause blood flow within the patient, and a controller operably coupled to the motor, the method comprising: determining, via the controller, a vascular pressure within the patient; determining, via the controller, a working voltage applied to the motor to cause the motor to rotate the impeller; determining, via the controller, a working speed of the motor caused by providing the working voltage to the motor; determining, via the controller, a blood flow parameter based on the vascular pressure, the working voltage, and the working speed; and determining, via the controller, a cardiac performance parameter based on the blood flow parameter.

In an Example 28, the method of Example 12, further comprising modifying operation of the percutaneous circulatory support device based on the cardiac performance parameter.

In an Example 29, the method of Example 12, further comprising determining, via the controller, contractibility of cardiac function of the patient by varying the working speed of the motor.

In an Example 30, the method of Example 12, further comprising segmenting, via the controller, waveforms of the working voltage.

In an Example 31, a percutaneous circulatory support device comprises: a housing configured to be positioned within a patient; an impeller carried within the housing; a motor configured to rotate the impeller relative to the housing to cause blood to flow through the housing; and a controller operably coupled to the motor, the controller being configured to determine: a working voltage applied to the motor to cause the motor to rotate the impeller; a blood flow parameter using a mathematical function comprising a square of the working voltage; and a cardiac performance parameter based on the blood flow parameter.

In an Example 32, the percutaneous circulatory support system of Example 16, wherein the controller is further configured to determine a vascular pressure within the patient, and the mathematical function further comprises a square of the vascular pressure.

In an Example 33, the percutaneous circulatory support system of Example 16, wherein the controller is further configured to determine a working speed of the motor caused by providing the working voltage to the motor, and the mathematical function further comprises a square of the working speed.

In an Example 34, the percutaneous circulatory support system of Example 16, wherein the controller is further configured to determine a vascular pressure within the patient, and the mathematical function further comprises a product of the vascular pressure and the working voltage.

In an Example 35, the percutaneous circulatory support system of Example 16, wherein the controller is further configured to determine: a vascular pressure within the patient; a working speed of the motor caused by providing the working voltage to the motor; and wherein the mathematical function further comprises a product of the vascular pressure, the working voltage, and the working speed.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
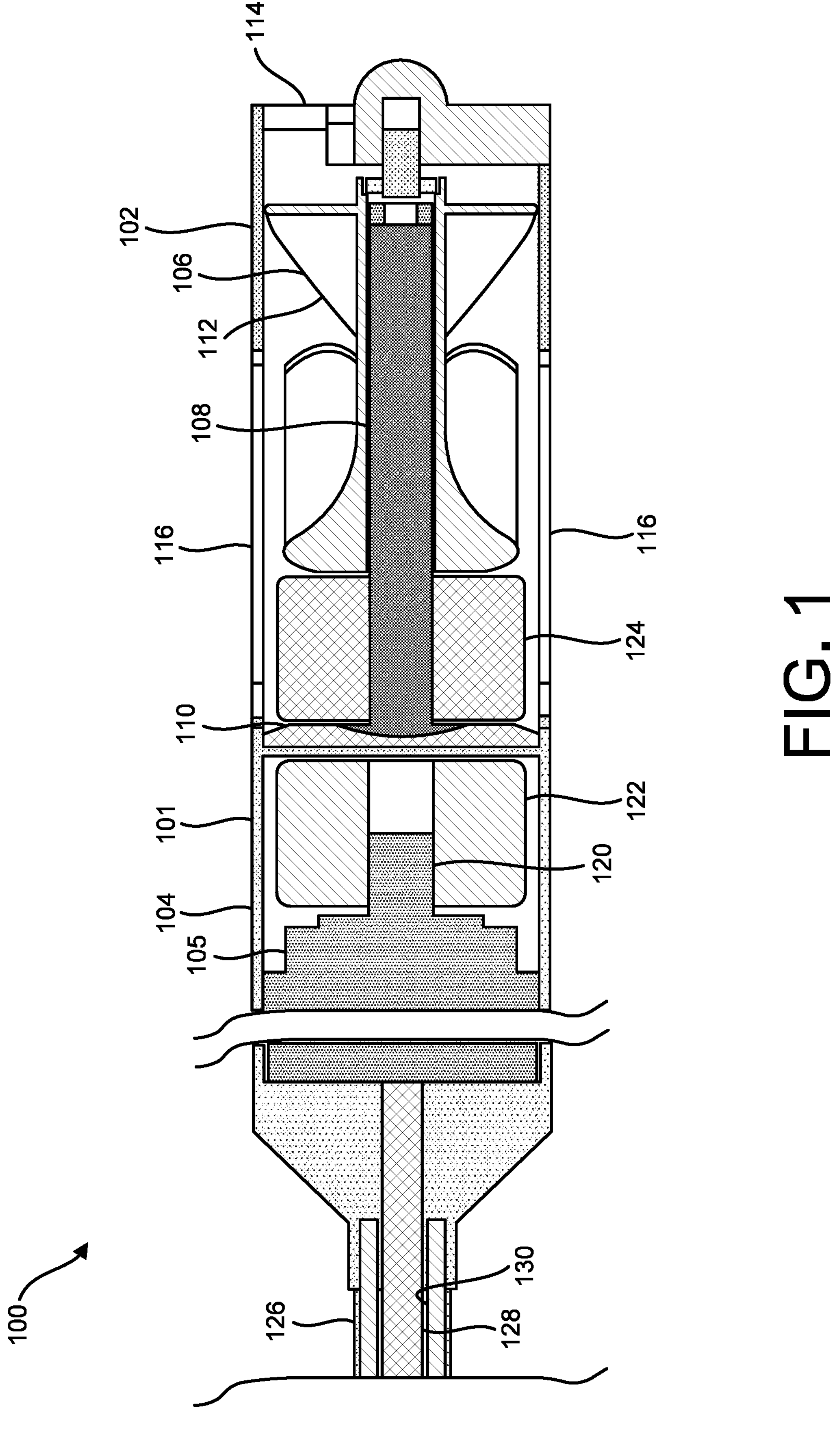
FIG. 1 is a side sectional view of an illustrative percutaneous circulatory support device (also referred to herein, interchangeably, as a "blood pump"), in accordance with embodiments of the subject matter disclosed herein.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 depicts a partial side sectional view of an illustrative percutaneous circulatory support device 100 (also referred to herein, interchangeably, as a "blood pump") in accordance with embodiments of the subject matter disclosed herein. The device 100 may form part of a percutaneous circulatory support system, together with, for example, a guidewire and an introducer sheath (not shown), among other devices. More specifically, the guidewire and the introducer sheath may facilitate percutaneously delivering the device 100 to a target location within a patient, such as within the patient's heart. Alternatively, the device 100 may be delivered to a different target location within a patient.

With continued reference to FIG. 1, the device 100 generally includes a housing 101 that includes an impeller housing 102 and a motor housing 104. In some embodiments, the impeller housing 102 and the motor housing 104 may be integrally or monolithically constructed. In other embodiments, the impeller housing 102 and the motor housing 104 may be separate components configured to be removably or permanently coupled. In some embodiments, the blood pump 100 may lack a separate motor housing 104 and the impeller housing 102 may be coupled directly to a motor 105 described below, or the motor housing 104 may be integrally constructed with the motor 105 described below.

The impeller housing 102 carries an impeller assembly 106 therein. The impeller assembly 106 includes an impeller shaft 108 that is rotatably supported by at least one bearing, such as a bearing 110. The impeller assembly 106 also includes an impeller 112 that rotates relative to the impeller housing 102 to drive blood through the device 100. More specifically, the impeller 112 causes blood to flow from a blood inlet 114 formed on the impeller housing 102, through the impeller housing 102, and out of a blood outlet 116 formed on the impeller housing 102. In some embodiments and as illustrated, the impeller shaft 108 and the impeller 112 may be separate components, and in other embodiments the impeller shaft 108 and the impeller 112 may be integrated. In some embodiment and as illustrated, the inlet 114 and/or the outlet 116 may each include multiple apertures. In other embodiments, the inlet 114 and/or the outlet 116 may each include a single aperture. In some embodiments and as illustrated, the inlet 114 may be formed on an end portion of the impeller housing 102 and the outlet 116 may be formed on a side portion of the impeller housing 102. In other embodiments, the inlet 114 and/or the outlet 116 may be formed on other portions of the impeller housing 102. In some embodiments, the impeller housing 102 may couple to a distally extending cannula (not shown), and the cannula may receive and deliver blood to the inlet 114.

With continued reference to FIG. 1, the motor housing 104 carries the motor 105, and the motor 105 is configured to rotatably drive the impeller 112 relative to the impeller housing 102. In the illustrated embodiment, the motor 105 rotates a drive shaft 120, which is coupled to a driving magnet 122. Rotation of the driving magnet 122 causes rotation of a driven magnet 124, which is connected to and rotates together with the impeller assembly 106. More specifically, in embodiments incorporating the impeller shaft 108, the impeller shaft 108 and the impeller 112 are configured to rotate with the driven magnet 124. In other embodiments, the motor 105 may couple to the impeller assembly 106 via other components.

The motor housing 104 couples to a catheter 126 opposite the impeller housing 102. The catheter 126 may couple to the motor housing 104 in various manners, such as laser welding, soldering, or the like. The catheter 126 extends proximally away from the motor housing 104. The catheter 126 carries a motor cable 128 within a main lumen 130, and the motor cable 128 may operably couple the motor 105 to a controller (shown elsewhere) and/or an power source (shown elsewhere).

Figure 2:
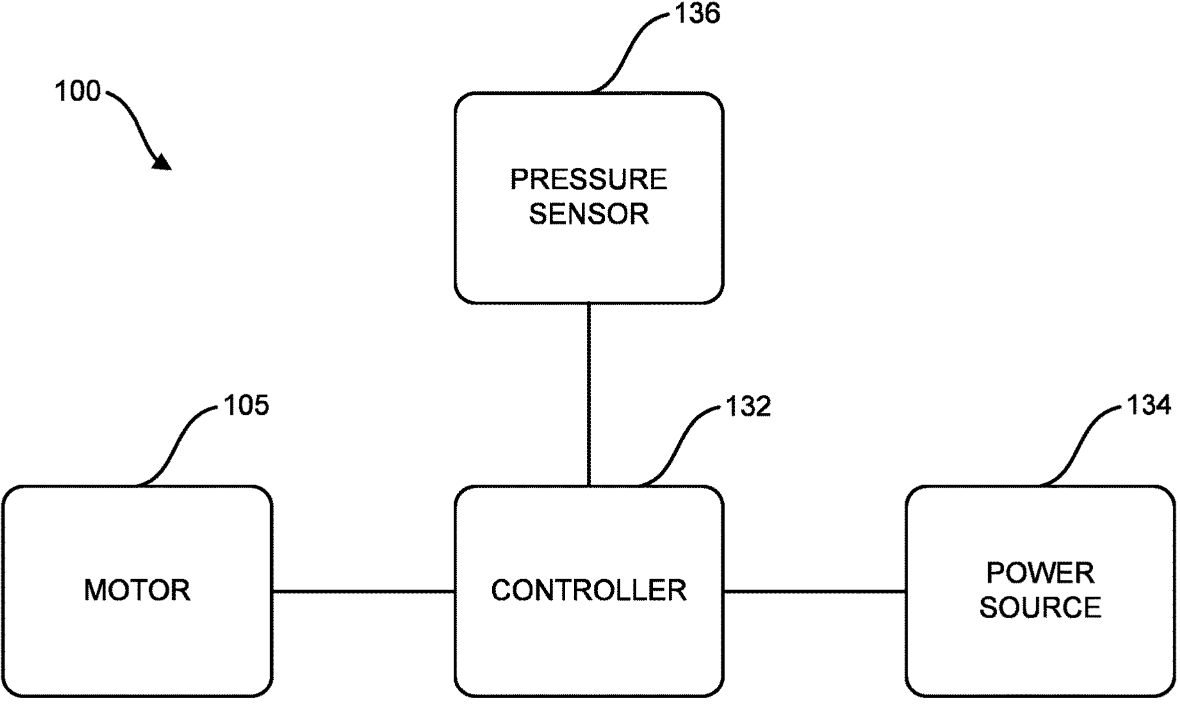
FIG. 2 is a schematic view of electronic components of the percutaneous circulatory support device of FIG. 1, in accordance with embodiments of the subject matter disclosed herein

With further reference to FIG. 1 and additional reference to FIG. 2, the controller 132 may be operably coupled to the motor 105 and configured to control the motor 105. In some embodiments, the controller 132 may be disposed within the motor housing 104. In other embodiments, the controller 132 may be disposed outside of the motor housing 104 (for example, in an independent housing, etc.) and coupled to the motor 105 via the motor cable 128. In some embodiments, the controller 132 may include multiple components, one or more of which may be disposed within the motor housing 104. According to embodiments, the controller 132 may be, may include, or may be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more Central Processing Units (CPUs), software, hardware, firmware, or any combination of these and/or other components. Although the controller 132 is referred to herein in the singular, the controller may be implemented in multiple instances, distributed across multiple computing devices, instantiated within multiple virtual machines, and/or the like. In other embodiments, the motor 105 may be controlled in other manners. The controller 132 operably couples to the power source 134.

A pressure sensor 136 may be operably coupled to the controller 132. The pressure sensor 136 measures fluid, i.e., blood, pressure within the heart or blood vessel of a patient ("vascular pressure"), for example, within the aorta. The pressure sensor 136 may be positioned on the outside or within the housing 101, or on the catheter 126. The pressure sensor 136 may be, for example, an optical or electrical pressure sensor. As described in further detail below, the controller 132 determines a vascular pressure within the patient via the pressure sensor 136.

Generally, the controller 132 is configured to determine one or more cardiac performance parameters based on one or more device performance parameters. Such device performance parameters may include, for example, the pressure sensed by the pressure sensor 136, the working voltage applied to the motor 105, and the working/output speed of the motor 105. The cardiac performance parameters may include, for example, cardiac output, cardiac power, left ventricular pressure, aortic pressure, heart rate, mean aortic pressure, systolic blood pressure, diastolic blood pressure, left-ventricular end diastolic pressure ("LVEDP"—the minimum pressure in the left ventricle, which can be correlated to a specific point in the pressure waveform of the device 100), pulse pressure, stoke volume, load state, and/or volume load state. The cardiac performance parameters, or changes thereof, can provide an indication of cardiac health. As such, the cardiac performance parameters may be provided to a medical practitioner (for example, via a display (not shown) operably coupled to the controller 132), and the medical practitioner may then modify device operation (for example, device position, motor working speed and, as a result, blood flow through the device 100) to modify patient treatment. Alternatively, the device 100 may automatically modify operation based on the cardiac performance parameters. More specifically, the device 100 may follow a predefined profile for reducing the support provided to the patient by the device 100.

Figure 3:
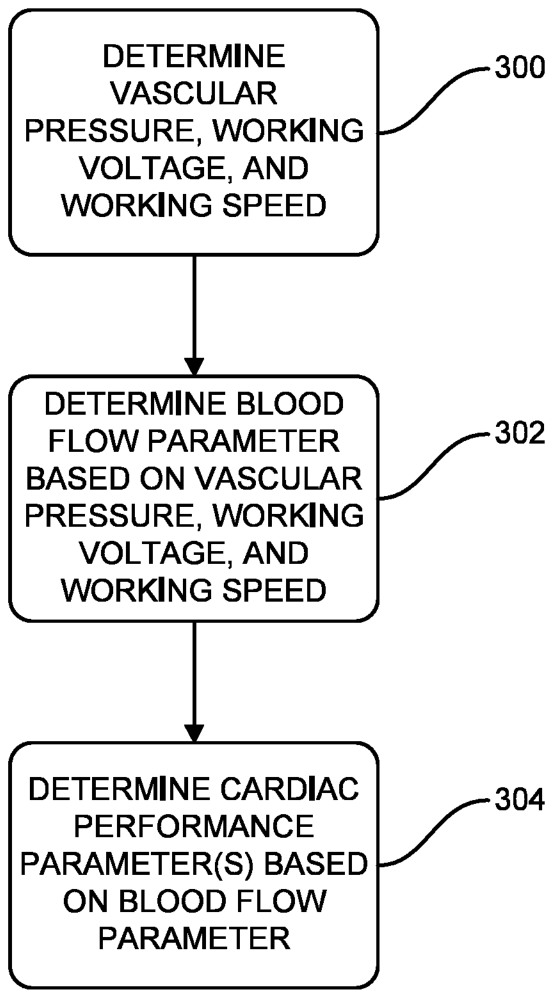
FIG. 3 is a flow diagram of an illustrative method of operating a percutaneous circulatory support device and determining one or more cardiac performance parameters of a patient, in accordance with embodiments of the subject matter disclosed herein.

Referring to FIG. 3, in some embodiments the controller 132 is configured to determine one or more cardiac performance parameters as follows. First, at block 300 the controller 132 determines one or more cardiac performance parameters, more specifically a vascular pressure within the patient, a working voltage applied to the motor 105, and the working speed of the motor 105. In some embodiments, the vascular pressure determined by the controller 132 is an aortic pressure. In some embodiments, the controller 132 determines the vascular pressure within the patient via the pressure sensor 136. In some embodiments, the controller 132 determines the working speed of the motor 105 by observing voltage fluctuations on the windings of the motor 105 using known techniques for controlling sensorless motors. Next, at block 302 the controller 132 inputs the pressure, the working voltage, and the working speed into a mathematical function to determine a blood flow parameter, such as the blood flow rate through the device 100. In some embodiments, the mathematical function is the sum of various terms including the pressure, the working voltage applied to the motor 105, and the working speed of the motor 105. Such terms may include the squares of the pressure, the working voltage, and/or the working speed, and/or the product of the pressure, the working voltage, and/or the working speed. More specifically, the function may be a polynomial function, such as:

$$\text{Flow} = (a_0 * p^2) + (a_1 * p) + (b_0 * v^2) + (b_1 * v) + (c_0 * s^2) + (c_1 * s + (d * p * v) + (e * p * s) + (f * v * s) + (g * p * v * s) + k$$

where Flow is the blood flow rate through the device 100, $a_0$, $a_1$, $b_0$, $b_1$, $c_0$, $c_1$, d, e, f, g, and k are coefficients, and p, v, and s are pressure, voltage, and speed, respectively. In some embodiments, the coefficients are based on the features of a particular pump, motor, and controller. The coefficients are also dependent on the units of measurement for the terms involved. Typically, the coefficients for higher order terms will be between −1 and 1, and the coefficients for first order terms may be larger. In some embodiments, the polynomial function may further include various higher order terms, but such terms do not significantly affect the calculated flow rate. Similarly, in some embodiments, the polynomial function may further include various exponential or trigonometric terms. Whether or not these additional terms should be included may be determined by comparing flow data collected in controlled tests with predicted flow; any difference between the two values is compared with available parameters or combinations thereof. At block 304, the controller 132 determines cardiac performance parameters using the calculated blood flow rate in addition to pressure. In particular, effects on cardiac output and cardiac power output can be estimated using aortic pressure and the additional blood flow provided by the pump. Such a determination may also be based on, sensed pressure, pulse, and anatomical data provided by the operator. The cardiac performance parameters may be, for example, any of the parameters listed hereinabove, and device operation may be modified based on the parameters.

In some embodiments, the controller 132 is configured to determine the contractibility of the cardiac function by varying the speed of the motor 105, more specifically by pulsing the speed of the motor 105 over a cycle (heartbeat) or a number of cycles. Once determined, contractibility contributes to the calculation of cardiac output power. That is, the device 100 effectively self-calibrates the determination of cardiac power during operation.

In some embodiments, the controller 132 is configured to segment voltage waveforms to isolate a cardiac cycle for analysis. The controller 132 may analyze the waveforms to determine if they substantially match a known model, which can indicate that the device 100 is properly positioned within a patient. The controller 132 may additionally or alternatively analyze the waveforms to determine if one or more portions thereof exceed thresholds, which can indicate occurrence of a pump blockage. More specifically, the steady state portion (near zero Hertz) of the voltage waveform can be used to detect a blocked blood inlet when the voltage drops below a threshold specific to a pump and impeller design.

In some embodiments, the motor 105 operates at a medical practitioner-selected speed, and the motor 105 is driven by a variable voltage to provide various levels of cardiac support. In other words, the practitioner selects a motor speed based on the observed cardiac performance and the practitioner's judgement on how much blood flow is required in addition to the unassisted cardiac output.

EXAMPLE

As a hypothetical example, the percutaneous circulatory support device 100 is positioned in a patient, more specifically, in both the aorta and the left ventricle and across the aortic valve. Next, the controller 132 determines a vascular pressure of 123 mmHg, a motor working voltage of 6.95V, and a motor working speed of 29000 RPM. Then the controller 132 determines a blood flow rate of 0.66 L/min, using the pressure, the working voltage, the working speed, and the following coefficients in the above function: $a_0$ is $4.4065*10^{-5}$ L/(min*mmHg$^2$), $a_1$ is $-2.0249*10^{-3}$ L/(min*mmHg), $b_0$ is $3.0318*10^{-1}$ L/(min*V$^2$), $b_1$ is 2.9707 L/(min*V), $c_0$ is $4.39*10^{-5}$ L/(min*RPM$^2$), $c_1$ is $-7.039*10^{-4}$ L/(min*RPM), d is $1.1678*10^{-2}$ L/(min*mmHg*V), e is $-3.5599*10^{-6}$ L/(min*mmHg*RPM), f is $-2.4583*10^{-4}$ L/(min*V*RPM), g is 0.0 L/(min*mmHg*V*RPM), and k is $7.1132*10^{-1}$ L/min. Using the calculated blood flow rate, the controller 132 determines the pump's impact on cardiac power output; which in this case is 0.66 L/min*90.3 mmHg/451.1=0.13 or 13% of normalized cardiac output power added to the patient's baseline cardiac output.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A percutaneous circulatory support device, comprising:

a housing configured to be positioned within a patient;

an impeller carried within the housing;

a motor configured to rotate the impeller relative to the housing to cause blood to flow through the housing; and a controller operably coupled to the motor, the controller being configured to determine:

a vascular pressure within the patient;

a working voltage applied to the motor to cause the motor to rotate the impeller;

a working speed of the motor caused by providing the working voltage to the motor;

a blood flow parameter based on the vascular pressure, the working voltage, and the working speed; and a cardiac performance parameter based on the blood flow parameter.

2. The percutaneous circulatory support system of claim 1, further comprising a pressure sensor operably coupled to the controller, wherein the controller is configured to determine the vascular pressure within the patient via the pressure sensor.

3. The percutaneous circulatory support system of claim 1, wherein the motor comprises a plurality of motor windings, and the controller is configured to determine the working speed of the motor based on voltage fluctuations in the plurality of motor windings.

4. The percutaneous circulatory system of claim 1, wherein the controller determines the blood flow parameter by using a mathematical function comprising the vascular pressure, the working voltage, and the working speed.

5. The percutaneous circulatory support system of claim 4, wherein the mathematical function comprises a square of the vascular pressure.

6. The percutaneous circulatory support system of claim 4, wherein the mathematical function comprises a square of the working voltage.

7. The percutaneous circulatory support system of claim 4, wherein the mathematical function comprises a square of the working speed.

8. The percutaneous circulatory support system of claim 4, wherein the mathematical function comprises a product of the vascular pressure and the working voltage.

9. The percutaneous circulatory support system of claim 4, wherein the mathematical function comprises a product of the vascular pressure and the working speed.

10. The percutaneous circulatory support system of claim 4, wherein the mathematical function comprises a product of the working voltage and the working speed.

11. The percutaneous circulatory support system of claim 4, wherein the mathematical function comprises a product of the vascular pressure, the working voltage, and the working speed.

12. A method of operating a percutaneous circulatory support device positioned in a patient, the device comprising an impeller, a motor configured to rotate the impeller to cause blood flow within the patient, and a controller operably coupled to the motor, the method comprising:

determining, via the controller, a vascular pressure within the patient;

determining, via the controller, a working voltage applied to the motor to cause the motor to rotate the impeller;

determining, via the controller, a working speed of the motor caused by providing the working voltage to the motor;

determining, via the controller, a blood flow parameter based on the vascular pressure, the working voltage, and the working speed; and determining, via the controller, a cardiac performance parameter based on the blood flow parameter.

13. The method of claim 12, further comprising modifying operation of the percutaneous circulatory support device based on the cardiac performance parameter.

14. The method of claim 12, further comprising determining, via the controller, contractability of cardiac function of the patient by varying the working speed of the motor.

15. The method of claim 12, further comprising segmenting, via the controller, waveforms of the working voltage.

16. A percutaneous circulatory support device, comprising:

a housing configured to be positioned within a patient;

an impeller carried within the housing;

a motor configured to rotate the impeller relative to the housing to cause blood to flow through the housing; and a controller operably coupled to the motor, the controller being configured to determine:

a working voltage applied to the motor to cause the motor to rotate the impeller;

a blood flow parameter using a mathematical function comprising a square of the working voltage; and a cardiac performance parameter based on the blood flow parameter.

17. The percutaneous circulatory support system of claim 16, wherein the controller is further configured to determine a vascular pressure within the patient, and the mathematical function further comprises a square of the vascular pressure.

18. The percutaneous circulatory support system of claim 16, wherein the controller is further configured to determine a working speed of the motor caused by providing the working voltage to the motor, and the mathematical function further comprises a square of the working speed.

19. The percutaneous circulatory support system of claim 16, wherein the controller is further configured to determine a vascular pressure within the patient, and the mathematical function further comprises a product of the vascular pressure and the working voltage.

20. The percutaneous circulatory support system of claim 16, wherein the controller is further configured to determine:

a vascular pressure within the patient;

a working speed of the motor caused by providing the working voltage to the motor; and wherein the mathematical function further comprises a product of the vascular pressure, the working voltage, and the working speed.

* * * * *